(12) United States Patent
Axelrod et al.

(10) Patent No.: US 7,515,963 B2
(45) Date of Patent: Apr. 7, 2009

(54) METHOD OF PATIENT INITIATED ELECTRO-CARDIOGRAM STORAGE, STATUS QUERY AND THERAPY ACTIVATION

(75) Inventors: Jay W. Axelrod, Minneapolis, MN (US); William R. Mass, Maple Grove, MN (US); Jason Malone, Lino Lakes, MN (US); Richard E. Stein, Edina, MN (US); Robert J. Gaskill, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 534 days.

(21) Appl. No.: 10/738,904

(22) Filed: Dec. 16, 2003

(65) Prior Publication Data

US 2005/0131479 A1 Jun. 16, 2005

(51) Int. Cl.
*A61N 1/37* (2006.01)

(52) U.S. Cl. ......................................... 607/32; 607/30

(58) Field of Classification Search ................. 607/32, 607/60, 30; 128/903
See application file for complete search history.

(56) References Cited

U.S. PATENT DOCUMENTS

| | | | |
|---|---|---|---|
| 3,952,750 A | 4/1976 | Mirowski et al. | |
| 4,086,916 A | 5/1978 | Freeman et al. | |
| 4,210,149 A | 7/1980 | Heilman et al. | |
| 4,295,474 A | 10/1981 | Fischell | |
| 4,323,074 A | 4/1982 | Nelms | |
| 4,365,290 A | 12/1982 | Nelms et al. | |
| 4,384,585 A | 5/1983 | Zipes | |
| 4,572,191 A | 2/1986 | Mirowski et al. | |
| 4,625,730 A * | 12/1986 | Fountain et al. | 607/4 |
| 4,809,697 A * | 3/1989 | Causey et al. | 607/31 |
| 5,207,219 A | 5/1993 | Adams et al. | |
| 5,282,837 A | 2/1994 | Adams et al. | |
| 5,311,449 A | 5/1994 | Adams | |
| 5,336,245 A | 8/1994 | Adams et al. | |
| 5,342,408 A | 8/1994 | deCoriolis et al. | |
| 5,350,404 A | 9/1994 | Adams et al. | |
| 5,464,432 A | 11/1995 | Infinger et al. | |
| 5,490,862 A * | 2/1996 | Adams et al. | 607/6 |
| 5,518,001 A * | 5/1996 | Snell | 600/510 |
| 5,578,063 A | 11/1996 | Bocek et al. | |
| 5,674,249 A | 10/1997 | de Coriolis et al. | |

(Continued)

OTHER PUBLICATIONS

Non-final Office Action dated Dec. 4, 2006, U.S. Appl. No. 10/438,734, 12 pgs.

(Continued)

*Primary Examiner*—Carl H Layno
*Assistant Examiner*—Brian T Gedeon
(74) *Attorney, Agent, or Firm*—Schwegman, Lundberg & Woessner, P.A.

(57) ABSTRACT

A handheld cardiac rhythm management device for use by a patient to request status information from an implantable pulse generating device and to request that the pulse generating device provide a rhythm altering shock to the patient's heart. The device includes a plurality of deadfront status indicator lamps on a front of a case that are visible to the patient when the controller is held in the patient's hand. The device also includes buttons on the front of the case and a telemetry circuit for bi-directional communication with the implantable pulse generating device.

21 Claims, 12 Drawing Sheets

U.S. PATENT DOCUMENTS

| | | | |
|---|---|---|---|
| 5,693,076 | A | 12/1997 | Kaemmerer |
| 5,720,770 | A | 2/1998 | Nappholz et al. |
| 5,755,737 | A | 5/1998 | Prieve et al. |
| 5,766,224 | A | 6/1998 | Alferness et al. |
| 5,931,857 | A | 8/1999 | Prieve et al. |
| 5,987,356 | A | 11/1999 | DeGroot |
| 5,999,851 | A | 12/1999 | White |
| 6,006,132 | A * | 12/1999 | Tacker et al. .................. 607/5 |
| 6,057,758 | A | 5/2000 | Dempsey et al. |
| 6,091,988 | A | 7/2000 | Warman et al. |
| 6,249,703 | B1 | 6/2001 | Stanton et al. |
| 6,400,990 | B1 * | 6/2002 | Silvian ........................ 607/60 |
| 6,727,814 | B2 | 4/2004 | Saltzstein et al. |
| 6,804,554 | B2 * | 10/2004 | Ujhelyi et al. ................ 607/6 |
| 6,821,249 | B2 | 11/2004 | Casscells, III et al. |
| 6,941,168 | B2 | 9/2005 | Girouard |
| 2002/0072733 | A1 | 6/2002 | Flaherty |
| 2002/0123672 | A1 * | 9/2002 | Christophersom et al. .. 600/300 |
| 2003/0055458 | A1 | 3/2003 | Hamilton et al. |
| 2003/0144711 | A1 | 7/2003 | Pless et al. |
| 2004/0210256 | A1 | 10/2004 | Musley et al. |
| 2004/0230246 | A1 | 11/2004 | Stein et al. |
| 2004/0230247 | A1 | 11/2004 | Stein et al. |

OTHER PUBLICATIONS

"Appeal Brief mailed Jul. 17, 2006 in U.S. Appl. No. 10/749,093", 20 pgs.

"U.S. Appl. No. 10/438,734 Advisory Action mailed Mar. 16, 2006", 3 pgs.

"U.S. Appl. No. 10/438,734 Advisory Action mailed Jun. 7, 2006", 3 pgs.

"U.S. Appl. No. 10/438,734 Final Office Action mailed Jan. 11, 2006", 6 pgs.

"U.S. Appl. No. 10/438,734 Final Office Action mailed Jun. 20, 2007", 13 pgs.

"U.S. Appl. No. 10/438,734 Non Final Office Action mailed Jun. 27, 2005", 10 pgs.

"U.S. Appl. No. 10/438,734 Non Final Office Action mailed Dec. 4, 2006", 12 pgs.

"U.S. Appl. No. 10/438,734 Response filed Mar. 3, 2006 to Final Office Action mailed Jan. 11, 2006", 10 pgs.

"U.S. Appl. No. 10/438,734 Response filed Oct. 26, 2005 to Non Final Office Action mailed Jun. 27, 2005", 9 pgs.

"U.S. Appl. No. 10/438,734 Response mailed Mar. 5, 2007 to Non Final Office Action mailed Dec. 4, 2006", 12 pgs.

"U.S. Appl. No. 10/749,093, Response filed Jan. 18, 2008 to Final Office Action mailed Oct. 22, 2007", 26 pgs.

"U.S. Appl. No. 10/749,093 Advisory Action mailed Mar. 31, 2006", 3 pgs.

"U.S. Appl. No. 10/749,093 Final Office Action mailed Feb. 22, 2006", 5 pgs.

"U.S. Appl. No. 10/749,093 Non Final Office Action mailed Apr. 27, 2007", 9 pgs.

"U.S. Appl. No. 10/749,093 Non Final Office Action mailed Jun. 27, 2005", 7 pgs.

"U.S. Appl. No. 10/749,093 Response filed Mar. 20, 2006 to Final Office Action mailed Feb. 22, 2006", 12 pgs.

"U.S. Appl. No. 10/749,093 Response filed Jul. 26, 2007 to Non Final Office Action mailed Apr. 27, 2007", 12 pgs.

"U.S. Appl. No. 10/749,093 Response filed Oct. 26, 2005 to Non Final Office Action mailed Jun. 27, 2005", 7 pgs.

"Final-Office Action Mailed Oct. 22, 2007 in U.S. Appl. No. 10/749,093", 12 pgs.

"Non-Final Office Action mailed Oct. 15, 2007 in U.S. Appl. No. 10/438,734, 13 pgs.", 13 Pages.

"Notice of Non-Complaint Appeal Brief mailed Aug. 7, 2006 in U.S. Appl. No. 10/749,093", 2 pgs.

"Notice of Panel Decision from Pre-Appeal Brief Review mailed Jun. 7, 2006 in U.S. Appl. No. 10/438,734", 2 pgs.

"Notice of Panel Decision from Pre-Appeal Brief Review mailed Jun. 15, 2006 in U.S. Appl. No. 10/749,093", 2 pgs.

"Pre-Appeal Brief mailed Apr. 19, 2006 in U.S. Appl. No. 10/749,093", 4 pgs.

"Pre-Appeal Brief mailed Apr. 3, 2006 in U.S. Appl. No. 10/438,734", 5 pgs.

"Request for Continued Examination mailed Jul. 7, 2006 in U.S. Appl. No. 10/438,734", 1 pg.

"Response to Notice of Non-Complaint Appeal Brief mailed Sep. 7, 2006 in U.S. Appl. No. 10/749,093", 22 pgs.

\* cited by examiner

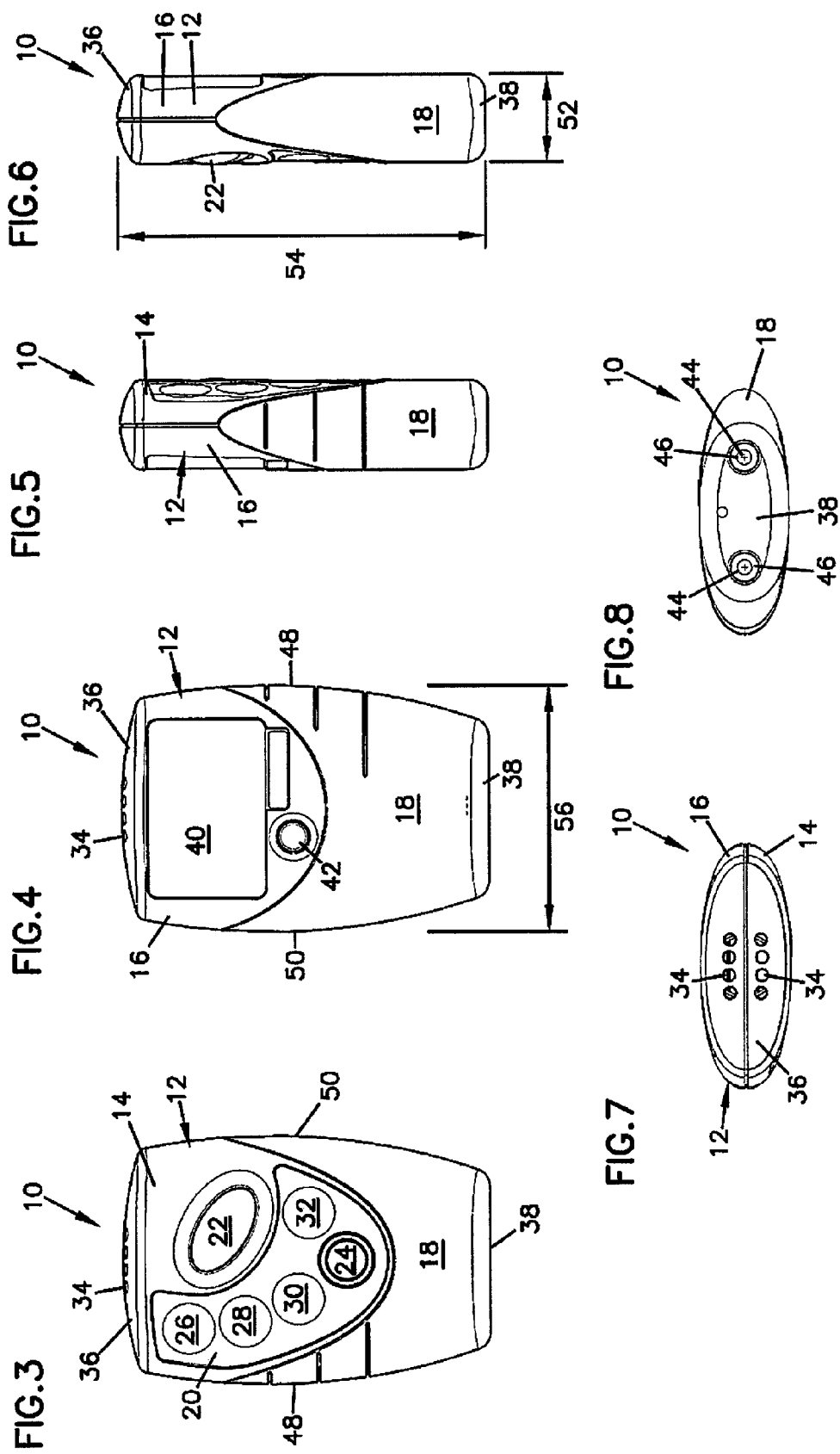

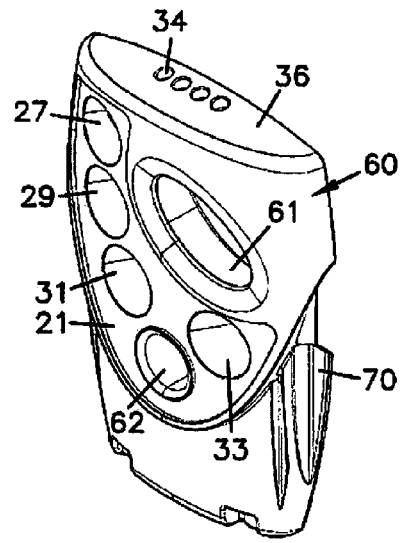
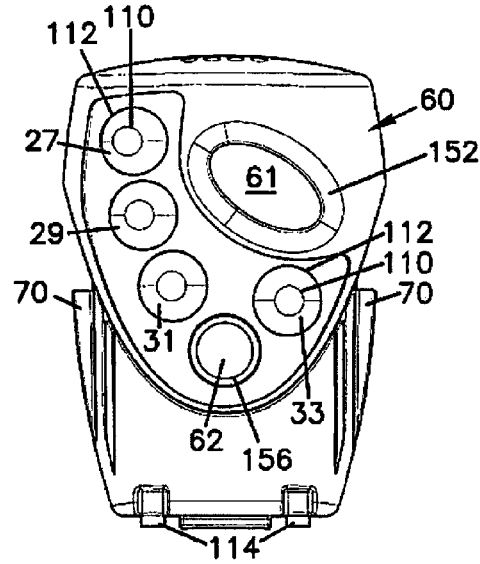
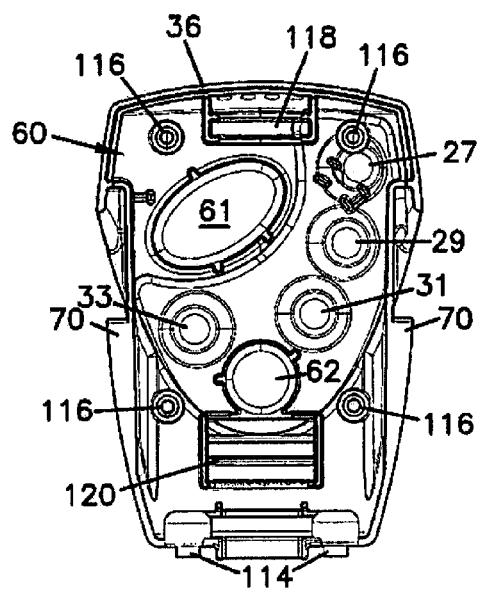

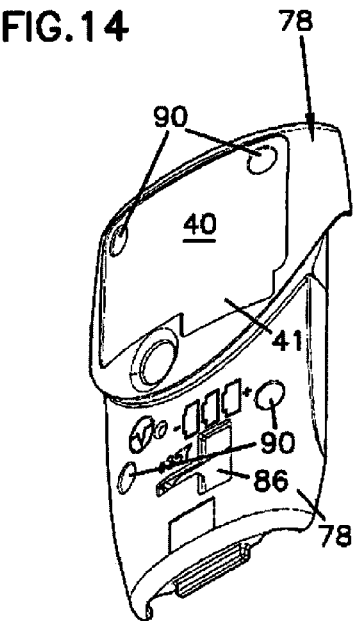
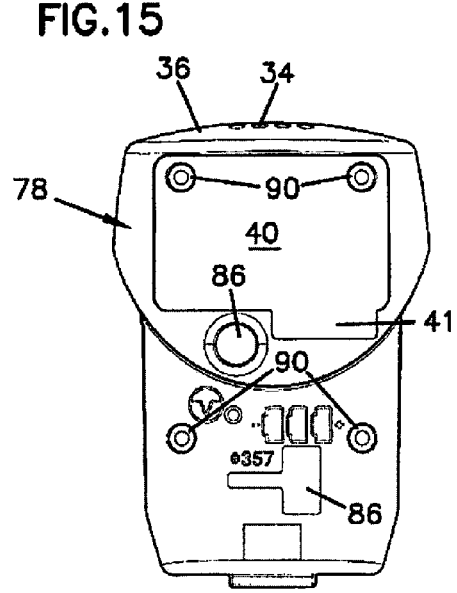
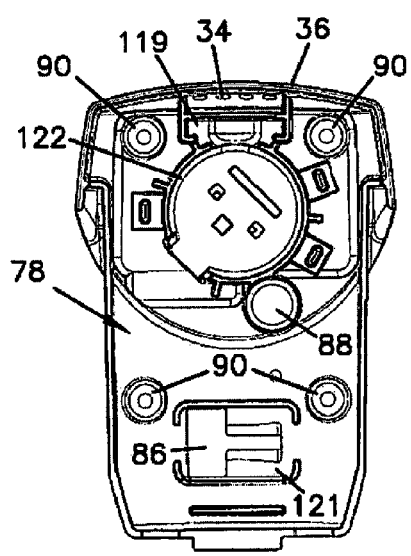

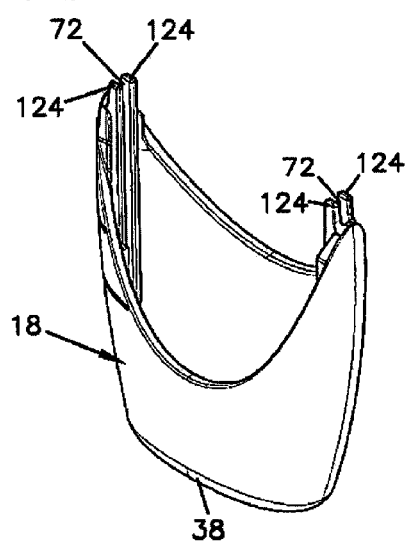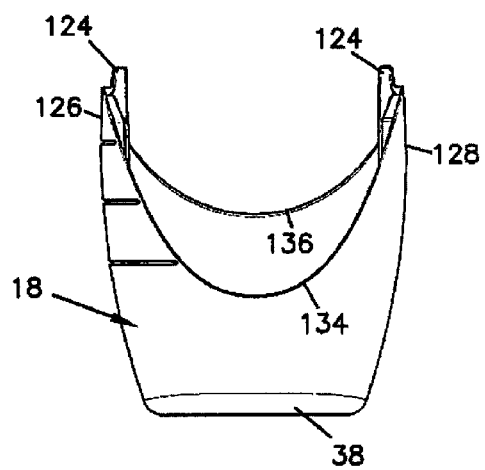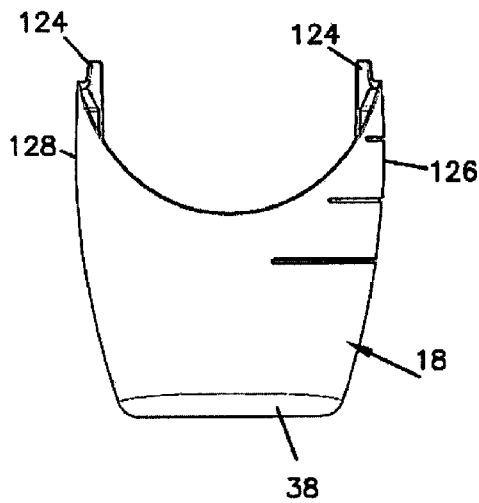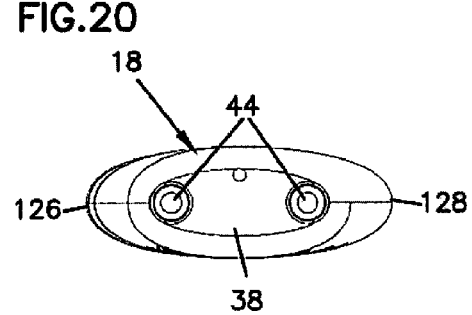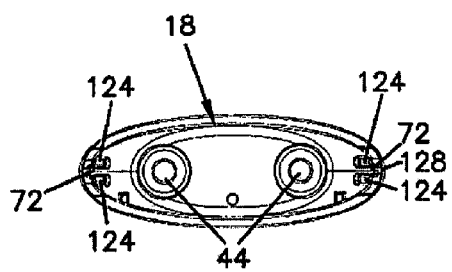

METHOD OF PATIENT INITIATED ELECTRO-CARDIOGRAM STORAGE, STATUS QUERY AND THERAPY ACTIVATION

FIELD OF THE INVENTION

The present invention relates generally to medical devices permitting patient controlled operation. More specifically, the present invention relates to devices permitting patient control over cardiac pacemaker functions.

BACKGROUND OF THE INVENTION

Implanted cardiac rhythm management devices are known for treating patients with cardiac rhythm problems. Such devices include circuitry for monitoring the contractions of a patient's heart and determining the need for a rhythm correction. Fast, slow or irregular heartbeat rhythms may signal the need for a rhythm correction. These implanted devices accomplish the rhythm correction by supplying an electrical current to the heart via one or more implanted electrical leads.

The rhythm management devices may also include a wireless sending and receiving capability that permits an external programmer or controller to send instructions and receive data from the implanted device. Such a controller permits communication with the implanted device without the need for physically accessing the implanted device. Such controllers are known for use by physicians or other medical personnel to monitor and control the function of an implanted device. Such controllers, with a more limited set of commands, are known to permit a patient to have some control over the function of an implanted device. Such known patient-operated controllers may require an electrical cord providing power from a wall outlet or other external power source and may include text based messages to communicate with the patient regarding the status of the implanted device and acknowledge receipt of an instruction by the implanted device.

Improvements to patient-operated controllers for use with implanted cardiac rhythm management devices are desirable.

SUMMARY OF THE INVENTION

The present invention relates to a method of permitting a patient to access certain functions of an implantable pulse generating device using a handheld controller. The handheld controller includes a case with a status query button, a therapy request button and a plurality of status indicators on a front of the case. The handheld controller also includes a self-contained power supply within the case and a telemetry circuit within the case for communicating with the implantable pulse generating device. The patient may request that a current heart rhythm be recorded by the implantable device.

The present invention further relates to a method of querying heart rhythm status using cordless self-contained handheld rhythm management device controller. A patient uses the handheld controller to send a signal to an implanted pulse generating device requesting current heart rhythm status. The implanted device responds to the signal from the handheld controller and provides information to the handheld controller. The controller displays the status information to the patient.

The present invention further relates to a method of requesting therapy from an implanted pulse generating device using a handheld cordless self-contained device controller. The patient uses the handheld controller to send a signal to the implanted pulse generating device requesting the implanted device to deliver a rhythm altering shock to the patient's heart. The implanted device responds to the shock request signal and provides status information to the handheld controller regarding current heart rhythm. The handheld controller displays the status information to the patient. The implanted device provides a rhythm altering shock to the patient's heart.

The present invention further relates to a method of preventing an implanted pulse generating device from delivering a rhythm altering shock using a handheld cordless self-contained device controller. The patient uses the handheld device to query the status of the implanted device and the implanted device responds to the status query indicating that a shock is being prepared. The patient uses the handheld device to signal the implanted device to not deliver the shock. The implanted device responds to the handheld device by stopping delivery of the shock and signaling the handheld controller that the shock has been stopped.

BRIEF DESCRIPTION OF THE DRAWINGS

The accompanying drawings, which are incorporated in and constitute a part of the description, illustrate several aspects of the invention and together with the detailed description, serve to explain the principles of the invention. A brief description of the drawings is as follows:

FIG. 3 is a front view of the handheld cardiac rhythm management device controller of FIG. 2.

FIG. 4 is a rear view of the handheld cardiac rhythm management device controller of FIG. 2.

FIG. 5 is a left side view of the handheld cardiac rhythm management device controller of FIG. 2.

FIG. 6 is a right side view of the handheld cardiac rhythm management device controller of FIG. 2.

FIG. 7 is a top view of the handheld cardiac rhythm management device controller of FIG. 2.

FIG. 8 is a bottom view of the handheld cardiac rhythm management device controller of FIG. 2.

FIG. 11 is a front perspective view of the front portion of the housing of the handheld cardiac rhythm management device controller of FIG. 9.

FIG. 12 is a front view of the front portion of the housing of FIG. 11.

FIG. 13 is a rear view of the front portion of the housing of FIG. 11.

FIG. 14 is a rear perspective view of the rear portion of the housing of the handheld cardiac rhythm management device controller of FIG. 9.

FIG. 15 is a rear view of the rear portion of the housing of FIG. 14.

FIG. 16 is a front view of the rear portion of the housing of FIG. 14.

FIG. 17 is a front perspective view of the cup of the housing of the handheld cardiac rhythm management device controller of FIG. 9.

FIG. 18 is a front view of the cup of the housing of FIG. 17.

FIG. 19 is a rear view of the cup of the housing of FIG. 17.

FIG. 20 is a bottom view of the cup of the housing of FIG. 17.

FIG. 21 is a top view of the cup of the housing of FIG. 17.

DETAILED DESCRIPTION

Reference will now be made in detail to exemplary aspects of the present invention which are illustrated in the accompanying drawings. Wherever possible, the same reference numbers will be used throughout the drawings to refer to the same or similar parts.

Figure 1:
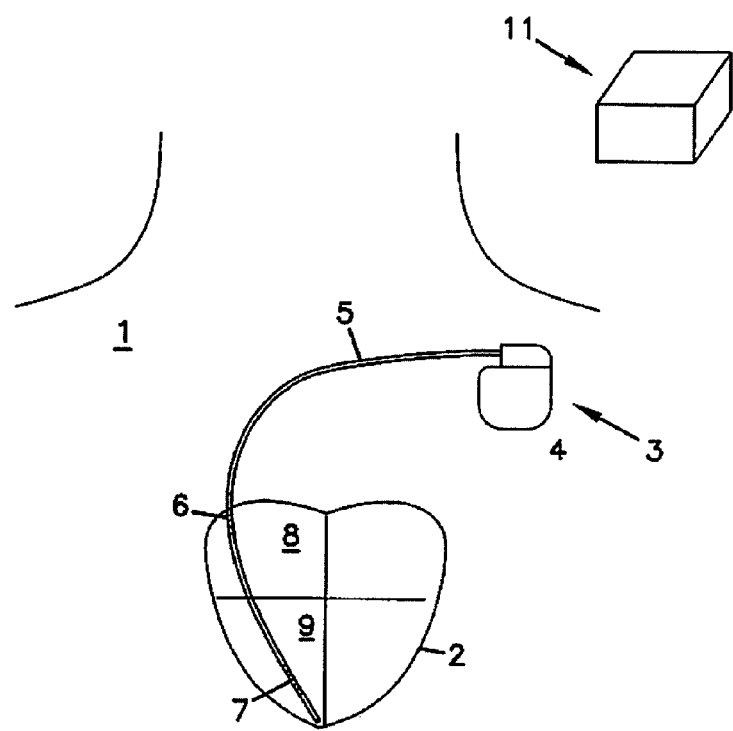
FIG. 1 is a schematic view of a portion of a patient's body illustrating the heart to which an implantable rhythm management device is linked and an external programmer for programming the implantable rhythm management device.

Referring now to FIG. 1, a patient's body 1 is illustrated and includes a heart 2 which may have experienced some degree of arrhythmic function. To sense and correct such arrhythmic function, an implantable cardiac rhythm management device 3 including a rhythm analysis and pulse generating unit 4 has been placed within body 1. Implantable rhythm management device 3 also includes a catheter 5 which electrically links heart 2 with rhythm analysis and pulse generating unit 4. Along catheter 5 may be located one or more electrodes such as electrodes 6 and 7 which may be inserted within one of heart chambers 8 and 9. This electrical connection between heart 2 and rhythm analysis and pulse generating unit 4 allows rhythm analysis and pulse generating unit 4 to sense electric fields relating to the contraction of the heart to determine a rhythm of heartbeat. Rhythm analysis and pulse generating unit 4 then evaluates the sensed rhythm to determine if heart 2 is functioning within a set of normal parameters. If rhythm analysis and pulse generating unit 4 determines that heart 2 is not within these normal parameters, unit 4 may deliver a series of correcting electrical shocks to chambers 8 and 9 of heart 2 to correct the rhythm.

Implantable rhythm management device 3 may be a pacemaker or defibrillator of the type disclosed in commonly-owned U.S. Pat. Nos. 5,999,851, 6,285,909 B1, 6,400,986 B1 and 6,415,175 B1. The disclosures of these patents incorporated herein by reference.

The physician or clinician treating a patient within whose body 1 implantable rhythm management device 3 has been implanted will use a programmer 11 with the capability to access and control all of the functions of the pacemaker. Such a physician-operated programmer is described in commonly-owned U.S. Pat. No. 6,522,925 B1, the disclosure of which is incorporated herein by reference.

Figure 2:
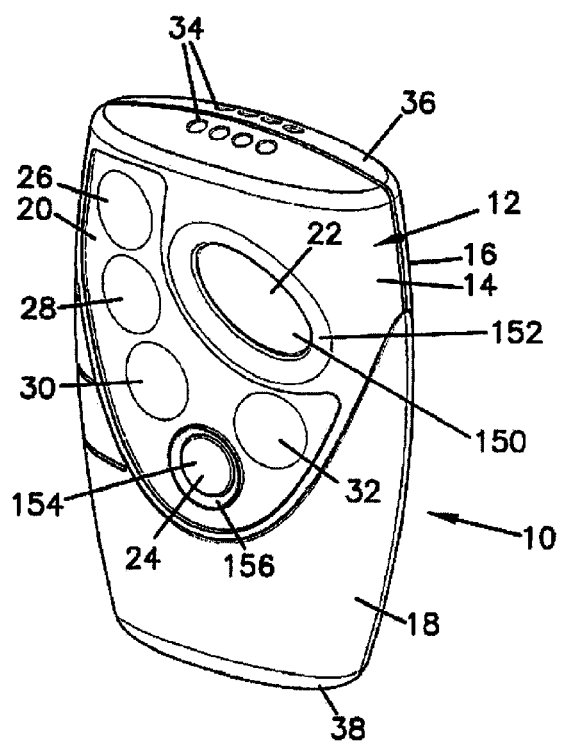
FIG. 2 is a front perspective view of a handheld cardiac rhythm management device controller according to the present invention.

Referring now to FIG. 2, a handheld cardiac rhythm management controller 10 is shown. Controller 10 is a patient-operated device which provides the patient with the capability to control over a limited set of the functions performed by implantable rhythm management device 3 for use with cardiac therapies. These capabilities are accessed using buttons and signal lights on a front 14 of a case 12 of controller 10. The buttons include a query button 22 and a therapy request button 24. The signal lights include four deadfront status indicators 26, 28, 30 and 32. These deadfront status indicators provide an indication of the status of implantable rhythm management device 3 with which controller 10 is communicating. The term deadfront is defined as meaning that the indicators denote status of a particular function or condition by being on or off and does not change shape, color or message to convey information. Another example of such deadfront status indicators are the warning lights incorporated into the dashboard of automobiles to indicate such things as oil pressure being below a preset limit, that the driver's seatbelt is unfastened, that the traction control system is operating, and similar conditions.

Deadfront status indicators 26, 28, 30 and 32 are lit from by behind (as will be discussed in further detail below with regard to FIG. 9) and are differentiated from one another by the use of uniquely colored and shaped icons. Further details of the icons associated with the status indicators is provided below in the discussion regarding FIG. 21.

Referring now to FIGS. 2 through 8, case 12 of controller 10 includes front 14, a rear 16, a top 36 and a bottom 38. Mounted about bottom 38 is a removable cup 18. In top 36 are a plurality of openings 34 through which audible signals and commands generated by controller 10 may be transmitted. Front 14 also includes an overlay 20. Overlay 20 includes status indicators 26, 28, 30 and 32. Status indicators 26, 28, 30 and 32 are light transmissive shapes in overlay 20. When illuminated from within case 12, as will be described below, they provide an indication to a patient visible from the front of controller 10 of status information communicated by implantable rhythm management device 3. The remainder of overlay 20 is generally not light transmissive so that the lamps within case 12 which light the status indicators do not shine through other portions of overlay 20. This ensures that each status indication will be unique and unambiguous.

On rear 16 is an area 40 for receiving a self-adhesive instruction label, providing information to the patient regarding the use and operation of controller 10. Beneath label area 40 on rear 16 is located a volume control button 42. Button 42 controls the volume of audible signals and commands generated by controller 10 and transmitted through the plurality of openings 34.

Bottom 38 includes a pair of fastener openings 46 into each of which is inserted a removable fastener such as screw 46. Screws 46 extend through openings 46 in cup 18 and engage threaded openings of case 12 to releasably hold cup 18 to controller 10. Cup 18 includes a left side 48 and a right side 50, which are shaped to fit comfortably within the patient's hand.

Controller 10 defines a depth 52 between the furthest extents of front 14 and rear 16, a height 54 between the furthest extents of top 36 and bottom 38, and a width 56 between the furthest extent of left side 48 and right 50. It is desirable that depth 52, height 54 and width 56 be in specific proportion to each other to fit comfortably within a patient's hand. The proportion or ratio between height 54 and depth 52 is preferably between 3.95 and 4.1 to 1, and most preferably approximately 4.03 to 1. The proportion or ratio between width 56 and depth 52 is preferably between defined between 2.65 and 2.8, and most preferably 2.72 to 1. Using average adult human hands, it has been determined that a depth of approximately 0.80 to 0.85 inches is preferable, with 0.827 inches the most preferred depth 52. Using these dimensions for depth 52, height 54 and width 56, controller 10 fits comfortably within an average sized adult hand and buttons 22 and 24 fall comfortably within the reach of the thumb of the hand holding controller 10. In addition, these dimensions encourage the device to be held within the palm in such an orientation that status indicators 26, 28, 30 and 32 are not obstructed by the thumb or fingers and are visible to the patient.

Figure 9:
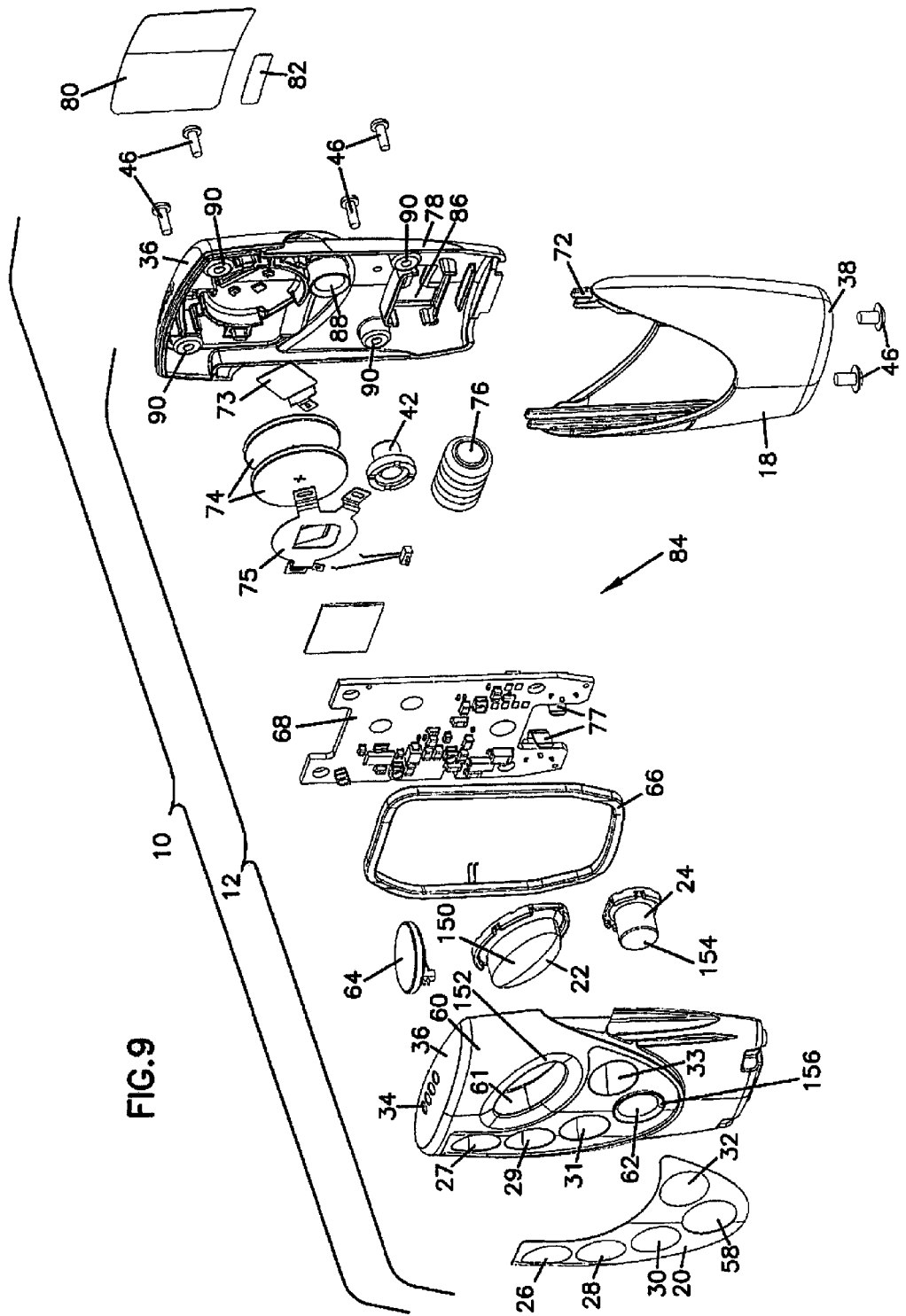
FIG. 9 is an exploded front perspective view of the handheld cardiac rhythm management device controller of FIG. 2.

Referring now to FIG. 9, a case front 60 and a case rear 78 cooperate to define case 12 and an interior 84. Overlay 20 includes an opening 58 to permit access to therapy request button 24 through a cooperating opening 62 in case front 60. Query button 22 extends through an opening 61 in case front 60. Behind each of the status indicators 26, 28, 30 and 32 of overlay 20 are lamp openings 27, 29, 31 and 33, respectively. The lamp openings permit lamps in the form of LEDs mounted to a circuit board 68 within interior 84 to illuminate the status indicators.

Captured between case front 60 and case rear 78 adjacent top 36 is a speaker 64, positioned beneath openings 34. Speaker 64 generates audible signals and commands to communicate status or to alert the patient. Mounted between circuit board 68 and case front 60 is a coil 66. Coil 66 is part of a wireless telemetry means of controller 10 permitting controller 10 to query and communicate with implantable rhythm management device 3.

Case front 60 includes a pair of opposing side rails 70. Rails 70 are received within slots 72 of cup 18 to position cup 18 about case 12. Fasteners 46 are then inserted through openings 44 in cup to hold cup 18 to case 12 and form bottom 38 of controller 10.

Circuit board 68 includes a pair of opposing battery contacts 77 between which are inserted batteries 76. Batteries 76 provide power to the visual and audible patient communication means (speaker 64 and status indicators 26, 28, 30 and 32) and electrical circuits associated with these communication means. Batteries 76 are replaceable by the user through an opening 86 in case rear 78. Between circuit board 68 and case rear 78 are telemetry batteries 74, which are inserted between a pair battery contacts 73 and 75. Batteries 74 provide power to the telemetry circuits which allow communication between controller 10 and implantable rhythm management device 3. These batteries are not user replaceable and may be expected to last the life of controller 10.

A button opening 88 in case rear 78 provides access to speaker volume button 42. Case rear 78 also includes a plurality of fastener openings 90 for receiving fasteners such as screws 46 which engage threaded openings 92 (shown in FIG. 13). An instruction label 80 is positioned within label space 40 on the rear of case rear 78. A unique identifier or serial number label 82 is also placed on the rear of case rear 78 below instruction label 80.

Figure 10:
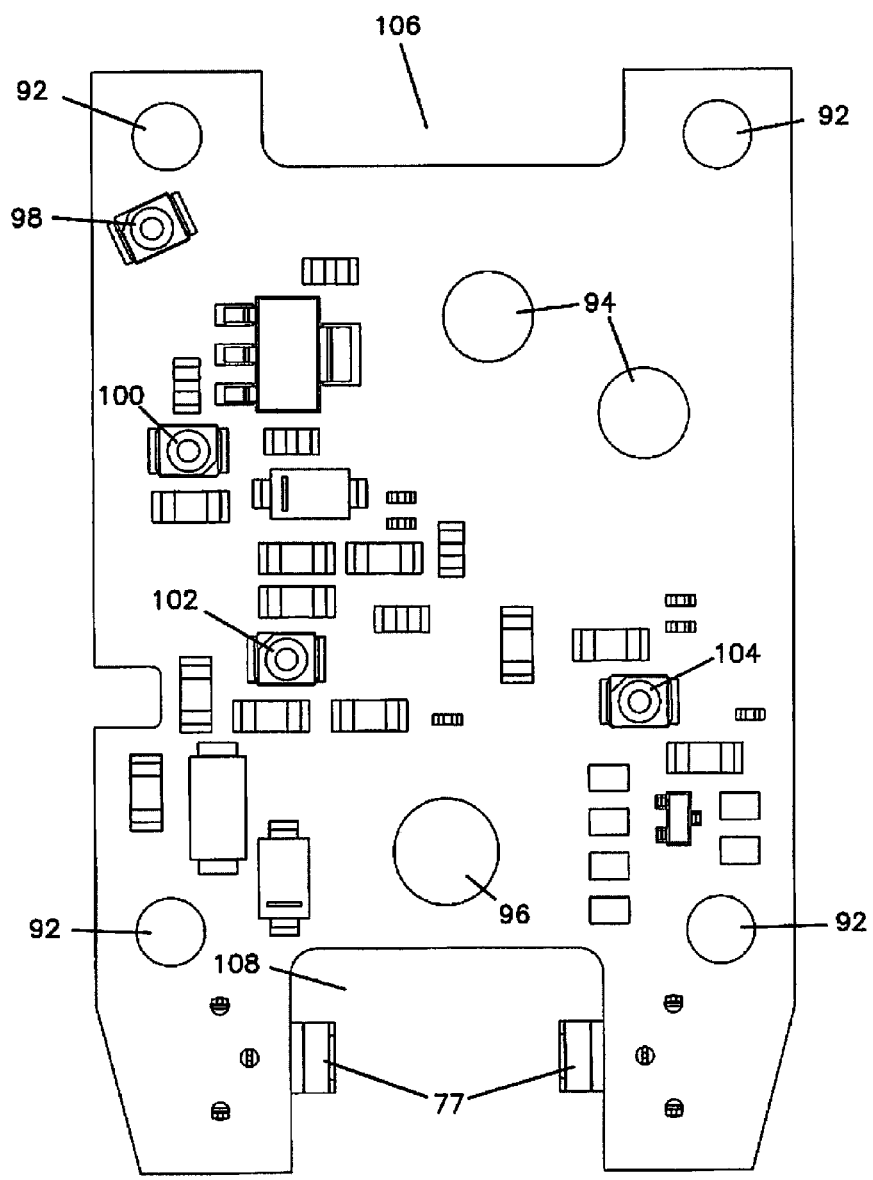
FIG. 10 is a front view of the circuit board of the handheld cardiac rhythm management device controller of FIG. 9.

Referring now to FIG. 10, circuit board 68 includes a plurality of holes 92 through the circuit board to permit fasteners 46 to extend from rear 16 through case rear 78 and engage case front 60. A pair of query contacts 94 are positioned on circuit board 68 beneath query button 22 and are activated when button 22 is pressed. A therapy request contact 96 is positioned on circuit board 68 beneath therapy request button 24 and is activated when button 24 is pressed. Four LEDs 98, 100, 102 and 104 are positioned on circuit board 68 beneath lamp openings 27, 29, 31 and 33, respectively, and when lit, illuminate status indicators 26, 28, 30 and 32, respectively. An upper recess 106 permits the installation of speaker 64 adjacent openings 34 in top 36. Battery contacts 77 are positioned within a lower recess 108 within which batteries 76 are positioned.

Utilizing deadfront status indicators in controller 10 reduces the amount of circuitry that must be mounted to circuit board 68. An alternative approach to communicating status and instructions to a patient might be through the use of a text-based display and message center. Such a text-based display would require additional circuitry on circuit board 68 to operate the display. In addition, such a display would require controller 10 to include a visually unobstructed area on front 14 to permit the patient to see and read the text messages. The ergonomics of controller 10 may need to be altered to reposition buttons 22 and 24 to accommodate the placement of such a text-based display. The overall size of controller 10 may need to be increased and shape altered to accommodate buttons 22 and 24 in their desired positions and permit placement of the text display in an unobstructed location. The utilization of appropriately positioned deadfront status indicators 26, 28, 30 and 32, in conjunction with a top mounted speaker to transmit audible instructions or messages permits case 12 of controller 10 to be advantageously sized and shaped while permitting circuit board 68 to be sized to fit within interior 84. The combination of the deadfront status indicators and the audible signals and instructions from speaker 64 provide the patient with sufficient feedback and information for the efficient operation of controller 10 with implantable rhythm management device 3. Alternatively, speaker 64 may be used to provide other, non-voice signals, such as tones or buzzes to communicate instructions or device status to the patient.

Referring now to FIGS. 11 through 13, case front 60 includes a recess 21 for receiving overlay 20. As can be seen in FIG. 12, each of the lamp openings 27, 29, 31 and 33 are cone-shaped with a narrow end 110 and a wide end 112. Narrow end 110 of each lamp opening is positioned adjacent the corresponding LED on circuit board 68 when assembled into a controller 10. These cone-shaped lamp openings serve to direct and focus the light from each LED behind the status indicator icon to which it corresponds to promote more uniform lighting of the icon and reduce bleed-over of light intended for one icon to an adjacent icon. Located in a lower edge of case front 60 is a pair of threaded inserts 114 for receiving fasteners 46 inserted through openings 44 in cup 18.

As shown in FIG. 13, a plurality of openings 116 are positioned to receive fasteners 46 inserted through openings 90 in case rear 78 and through holes 92 in circuit board 68 to releasably fasten case front 60 to case rear 78. A slot 118 is formed adjacent top 36 to permit the mounting of speaker 64 adjacent openings 34. A structure 120 aids in the positioning of batteries 76 between battery contacts 77.

Referring now to FIGS. 14 through 16, case rear 78 includes a portion 41 of recess 40 to receive serial number label 82 adjacent instruction label 80. Case rear 78 includes a slot 119 which cooperates with slot 118 to position speaker 64. Case rear 78 also includes a structure 121 about battery insertion opening 86. Structure 121 cooperates with structure 120 to position batteries 76 between battery contacts 77. Case rear 78 also includes circular wall structure 122 which aids in the positioning and holding of telemetry batteries 74 within controller 10.

Referring now to FIGS. 17 through 21, slots 72 of cup 18 are formed by a pair of rails 124 adjacent each of a left side 126 and a right side 128. It is anticipated that case front 60 and case rear 78 will be formed from a relatively hard plastic to aid in the durability and structural integrity of controller 10. It is anticipated that cup 18 will be made of a plastic material of a lower durometer to improve the comfort of the patient when gripping controller 10. The material of cup will also preferably have a higher coefficient of friction than case 12 to improve the ability of a patient to maintain a grip on controller 10. To encourage placement of controller 10 within a patient's hand in the correct orientation, only cup 18 would be made of a softer material.

Cup 18 includes a low scooped front 134 and a low scooped rear 136. Scooped front 134 and rear 136 permit left side 126 and right side 128 of cup 18 to extend up left side 48 and right 50 of controller 10 without limiting the space available on front 14 and rear 16 for the placement of status indicators 26, 28, 30 and 32, and buttons 22, 24 and 42. The upward extension of sides 126 and 128 extends the lower durometer material of cup 18 along sides 48 and 50 provides an improved grip surface for a patient. Additionally, such lower durometer material may provide a cushioning effect in the event controller 10 is dropped. Construction of controller 10, as indicated in the FIGS., places the center of gravity in the lower portion of case 12, and cup 18 is fitted about the lower portion of case 12. Thus, cup 18 of controller 10 will tend to impact first in the event of an accidental drop.

Figure 22:
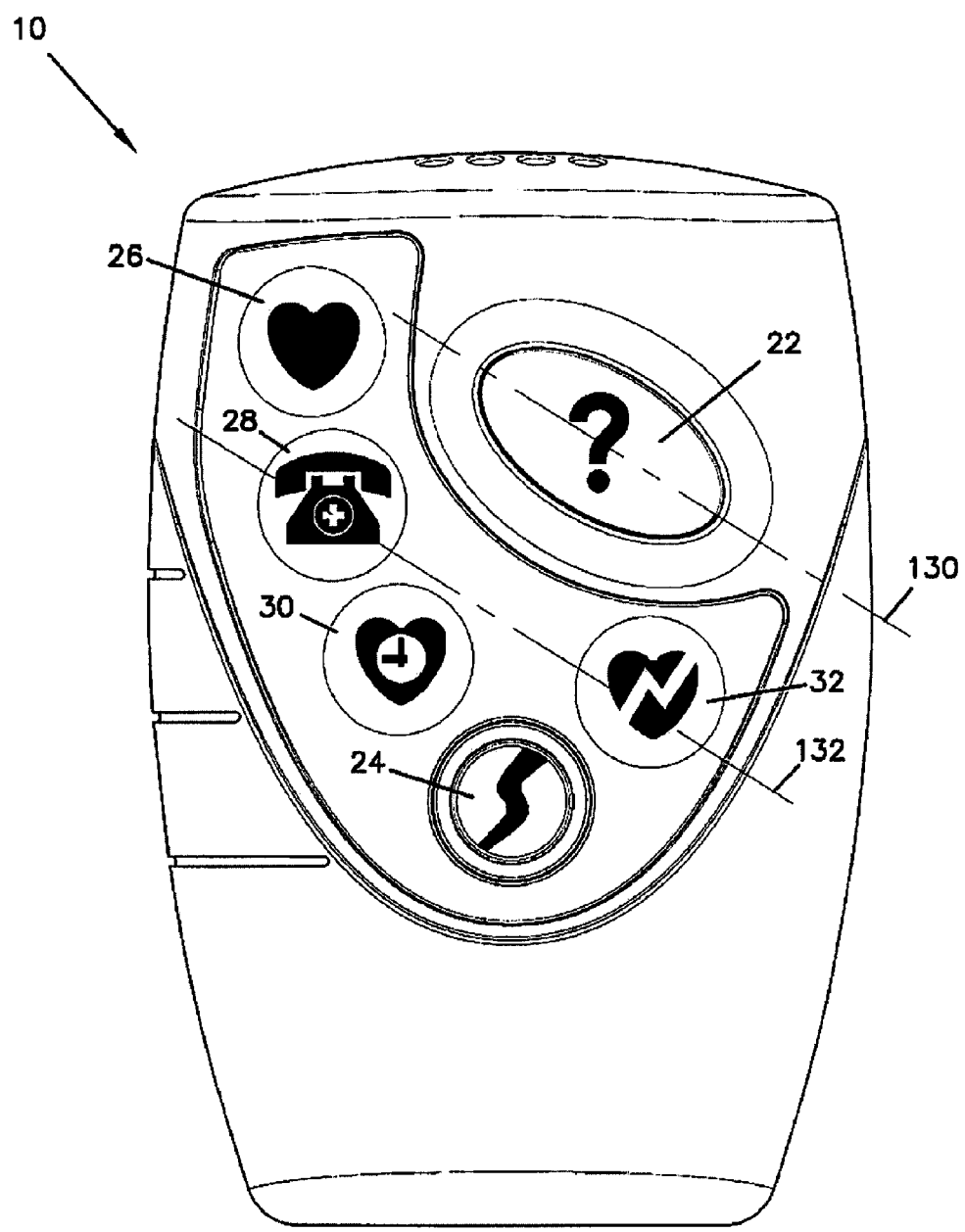
FIG. 22 is a front view of the handheld cardiac rhythm management device controller of FIG. 2, showing the status indicators on the front of the device.

Referring now to FIG. 22, the icons associated with each of the status indicators 26, 28, 30 and 32 are shown. Status indicator 26 is associated with an "In Normal Rhythm," green colored icon in a heart shape. Status indicator 26 is illuminated by LED 98 when controller 10 has queried implantable rhythm management device 3 and received confirmation that the current heart rhythm is within acceptable parameters. When status indicator 26 is lit, no other status indicators are illuminated.

Status indicator 28 is associated with a "Call Doctor," red colored icon shaped like a telephone with a cross in the center of the base unit. Status indicator 28 is illuminated by LED 100 when controller 10 has queried implantable rhythm management device 3 and received a warning that some function of the device or the heart rhythm are beyond acceptable parameters. The illumination of status indicator 28 indicates to the patient that he/she should contact a doctor immediately. When status indicator 28 is lit, no other status indicators are illuminated.

Status indicator 30 is associated with a "Therapy Pending," orange color icon shaped like a heart with a clock face positioned within the heart. Status indicator 30 is illuminated by LED 102 when controller 10 has queried implantable rhythm management device 3 and received information from implantable rhythm management device 3 that therapy (in the form of a rhythm modifying shock) has been scheduled by implantable rhythm management device 3. When status indicator 30 is lit, no other status indicators are illuminated.

Status indicator 32 is associated with a "Not In Normal Rhythm," yellow colored icon in the shape of a heart with a sharp jagged line extending across the heart. Status indicator 32 is illuminated by LED 104 when controller 10 has queried implantable rhythm management device 3 and received indication from implantable rhythm management device 3 that the heart is experiencing rhythm outside of normal rhythm parameters. When this condition is indicated by controller 10, it also indicates to the patient that the implantable rhythm management device 3 has not yet scheduled therapy to address this out-of-normal rhythm condition. When status indicator 32 is lit, no other status indicators are illuminated.

Query button 22 is associated with an icon including a blue background with a white question mark positioned in the middle of the background. Button 22 may be pressed by a patient to initiate a query of implantable rhythm management device 3 as to the current status of the implantable rhythm management device 3, any scheduled therapy and the current heart rhythm. No backlighting or illumination of button 22 is provided. Button 22 is oval in shape and defines a major axis 130. Major axis 130 is angled on front 14 of controller 10 at an angle generally parallel to a centerline 132 defined by a center of status indicator 28 and a center of status indicator 32.

In response to a patient pressing query button 22, controller 10 receives and displays the information received from implantable rhythm management device 3 as described above with regard to status indicators 26, 28, and 32.

Therapy request button 24 is associated with an icon including a yellow background with a soft lightning bolt line in black extending across the background. Button 24 may be pressed by a patient to initiate a therapy request. Upon the patient's pressing of button 24, controller 10 queries an implantable rhythm management device 3 to determine the status of the device, any scheduled therapy and the current heart rhythm, similar to the query performed when button 22 is pressed. Controller 10 may receive an indication from the implantable rhythm management device 3 that one of several conditions described below exists in response to the therapy request and illuminate the appropriate status indicator and associated icon.

Buttons 22 and 24 are positioned on front 14 of controller 10 to facilitate single handed use of controller 10 to access functions or query the status of implantable rhythm management device 3. While controller 10 is ergonomically equally suited for gripping in a patient's right or left hand, buttons 22 and 24 are more optimally suited gripping controller 10 is a patient's right hand. So held, buttons 22 and 24 are well suited for actuation by the patient's right thumb without the thumb obstructed visibility of the status indicator or blocking any openings 34, which may muffle audible messages and instructions (described in further detail below).

If controller 10 receives an indication that the patient's heart currently is within normal rhythm parameters, status indicator 26 and the "In Normal Rhythm" icon will be illuminated. No rhythm correction therapy will be scheduled.

If controller 10 receives an indication that the patient's heart currently is at a faster than normal rhythm but within a range that implantable rhythm management device 3 has been programmed to treat, status indicator 30 and the "Therapy Pending" icon will be illuminated. This signals to the patient that a shock will be delivered by implantable rhythm management device 3 to bring the heart back within normal rhythm parameters.

If controller 10 receives an indication that the patient's heart is beating fast but is within a range of rhythm parameters that implantable rhythm management device 3 has not been programmed to treat, status indicator 32 and the "Not In Normal Rhythm" icon will be illuminated. No rhythm correction therapy will be scheduled.

If controller 10 receives an indication that the implantable rhythm management device 3 has sensed a condition that requires the intervention of a doctor, status indicator 28 and the "Contact Doctor" icon will be illuminated. No rhythm correction therapy will be scheduled.

A patient may also use query button 22 to request that implantable rhythm management device 3 record a current heart rhythm. To initiate such a rhythm recording, the patient presses the query button and waits to see which icon will illuminate. If status indicator 26 and the "In Normal Rhythm" icon illuminates, the patient may then press query button 22 again to signal implantable rhythm management device 3 to record the current rhythm. This recorded rhythm may then be downloaded by the patient's doctor for later review and analysis.

If controller 10 illuminates status indicator 32 and the "Not In Normal Rhythm" icon in response to a press of the query button, this indicates to the patient that implantable rhythm management device 3 is recording the current heart rhythm.

Controller 10 may also illuminate status indicator 28 and the "Contact Doctor" icon in response to information received from implantable rhythm management device 3. Based on the capabilities of implantable rhythm management device 3, and also the programming performed by physician controller 11, implantable rhythm management device 3 may or may not be recording the current rhythm if status indicator 28 is illuminated.

If a patient wishes to stop a pending therapy by implantable rhythm management device 3, both query button 22 and therapy request button 24 may be depressed simultaneously and released. Controller 10 will then attempt to communicate with implantable rhythm management device 3 to stop the therapy. If a scheduled therapy has been stopped, the patient may elect to initiate the therapy at a later time, using the therapy request procedure described above.

In addition to the visible status indications described above, controller 10 may also provide audible status indications and instructions utilizing speaker 64. Such audible signals from speaker 64 are in response to pressing of buttons 22 and 24, and in response to information received from implantable rhythm management device 3. Examples of such audible signals are described below.

When a patient presses query button 22 to request the status of implantable rhythm management device 3, speaker 64 may transmit an audible human or synthesized voice with the acknowledgement "Status requested," followed by the instruction, "Locate implanted device." This indicates to the patient that controller 10 should be positioned adjacent implantable rhythm management device 3 so that controller 10 may receive information from implantable rhythm management device 3.

When a patient presses therapy request button 24 to request a shock be delivered, speaker 64 may transmit an audible human or synthesized voice with the acknowledgement "Shock requested," followed by the instruction, "Locate implanted device." This indicates to the patient that controller 10 should be positioned adjacent implantable rhythm management device 3 so that controller 10 may receive information from implantable rhythm management device 3.

Once controller 10 has been positioned with respect to implantable rhythm management device 3 and establishes communication with it, controller 10 will display the status information received, as described above with regard to the status indicators. If implantable rhythm management device 3 signals to controller 10 that the current rhythm is within normal parameters, speaker 64 may transmit the message "Rhythm is OK," in response to the pressing of either button. In either situation, status indicator 26 will also be illuminated.

If implantable rhythm management device 3 signals to controller 10 that the current heart rhythm is too fast for normal parameters but within the range of rhythm treatable by implantable rhythm management device 3, speaker 64 may transmit the message, "Rhythm is fast," in response to the pressing of query button 22. Status indicator 32 will also be illuminated.

If implantable rhythm management device 3 signals to controller 10 that the current heart rhythm is too fast for normal parameters but within the range of rhythm treatable by implantable rhythm management device 3, speaker 64 may transmit the message, "Rhythm is fast," and "Prepare for shock," in response to the pressing of therapy request button 24. Status indicator 30 will also be illuminated, indicating that implantable rhythm management device 3 has scheduled a shock.

If implantable rhythm management device 3 signals to controller 10 that the current heart rhythm is too fast for normal parameters but outside of the range of rhythm treatable by implantable rhythm management device 3, speaker 64 may transmit the message, "Rhythm is fast. Rhythm not treatable," in response to the pressing of either query button 22 or therapy request button 24. Status indicator 32 will also be illuminated.

If a patient wishes to stop a scheduled therapy, and presses both buttons 22 and 24 simultaneously, speaker 64 may transmit the message, "Shock stop requested," followed by the instruction, "Locate implanted device." Once controller 10 is positioned adjacent to implantable rhythm management device 3 and transmitted the instruction to stop the scheduled therapy, speaker 64 may transmit the message, "Shock is stopped." If implantable rhythm management device 3 still senses that the heart rhythm is faster than the normal parameters but within the range for which implantable rhythm management device 3 may provide therapy, speaker 64 may also transmit the message, "Rhythm is fast."

If query button 22 has been pressed a second time, indicating the patient wishes to have implantable rhythm management device 3 record the current rhythm after receiving the status indication from the first press of button 22, speaker 64 may transmit the message, "Rhythm recording requested," followed by the instruction, "Locate implanted device." Once implantable rhythm management device 3 has recorded the rhythm and communicated this to controller 10, speaker 64 may transmit the message, "Rhythm recorded."

If status indicator 28 is illuminated in response to the patient pressing either of buttons 22 or 24, speaker 64 may transmit the message, "Contact your physician".

If status indicator 26 is illuminated in response to the patient pressing either of buttons 22 or 24, speaker 64 may transmit the message, "Rhythm is OK. Patient control not available." This indicates that because the heart rhythm sensed by implantable rhythm management device 3 is within normal rhythm parameters, the patient will not be permitted to initiate a therapy request.

A physician may program implantable rhythm management device 3 so that patient initiated therapy is not possible for certain conditions of fast rhythm, even though the rhythm is within the range treatable with implantable rhythm management device 3. If implantable rhythm management device 3 is so programmed, and if the heart rhythm is within the range where patient initiated therapy is excluded, status indicator 32 may be illuminated in response to the patient pressing either of buttons 22 or 24, indicating that the current rhythm is faster than normal parameters. In this situation, speaker 64 may transmit the message, "Rhythm is fast. Patient control not available."

Speaker volume button 42 in rear 16 of controller 10 toggles speaker 64 between two or more different levels of volume. If the patient presses button 42 to toggle speaker 64 to zero volume, speaker 64 may transmit the message, "Speaker off." If the patient presses button 42 to toggle speaker 64 to an audible volume, speaker 64 may transmit a tone or other sound at a volume corresponding to the currently set volume of speaker 64, indicating to the patient approximately the volume level of the speaker.

Figure 23:
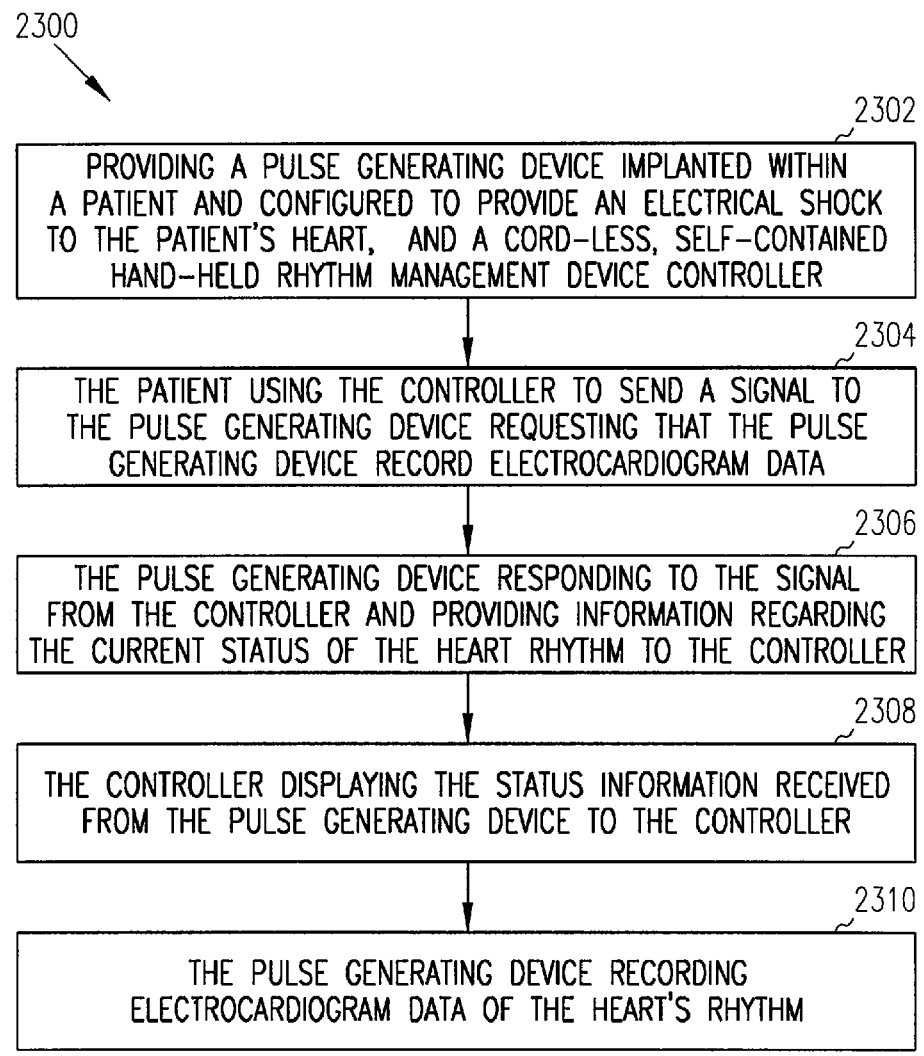
FIG. 23 is a flowchart illustrating a method of recording electrocardiogram data.

FIG. 23 is a flowchart illustrating a method 2300 of recording electrocardiogram data. At 2302, a pulse generating device and a cord-less, self contained hand-held rhythm management device controller are provided, the pulse generating device being implanted within a patient and configured to provide an electrical shock to the patient's heart. At 2304, the patient uses the controller to send a signal to the pulse generating device requesting that the pulse generating device record electrocardiogram data. At 2306, the pulse generating device responds to the signal from the controller and providing information regarding the current status of the heart rhythm to the controller. At 2308, the controller displays the status information received from the pulse generating device to the controller. At 2310, the pulse generating device records electrocardiogram data of the heart's rhythm. In an embodiment, the status information from the pulse generating device indicates that the heart's rhythm is within normal parameters and the pulse generating device records electrocardiogram data after receiving the signal from the controller. In an embodiment, the status information from the pulse generating device indicates that the heart's rhythm is outside of normal parameters and the pulse generating device has begun recording electrocardiogram data prior to receiving the signal from the controller. In an embodiment, the controller further communicates the status information to the patient by an audible human or synthesized voice through a speaker mounted within a case of the controller. In an embodiment, the controller displays the status information that the current heart rhythm is within normal parameters by illuminating an icon visible to the patient on a front of the controller. In an embodiment, the controller further communicates the status information to the patient by an audible human or synthesized voice through a speaker mounted within a case of the controller. In an embodiment, the controller displays the status information that the current heart rhythm is outside normal parameters by illuminating an icon visible to the patient on a front of the controller.

Figure 24:
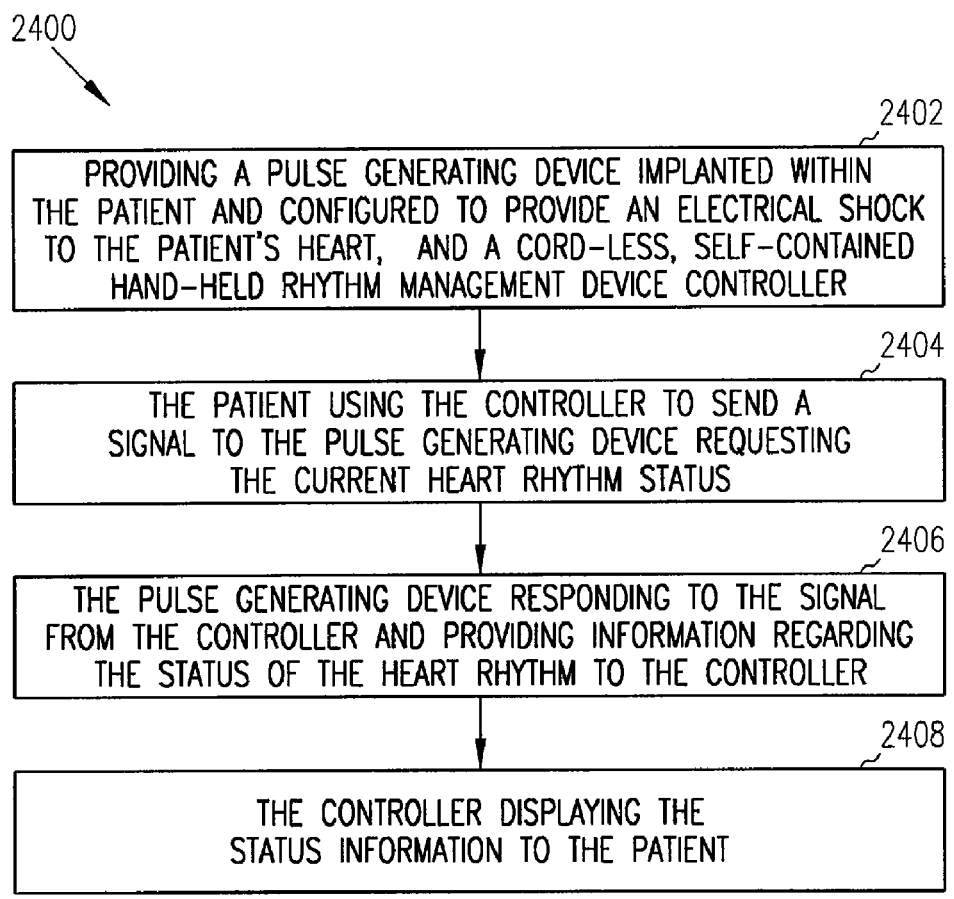
FIG. 24 is a flowchart illustrating a method of querying a status of a heart rhythm of a patient.

FIG. 24 is a flowchart illustrating a method 2400 of querying a status of a heart rhythm of a patient. At 2402, a pulse generating device and a cord-less, self contained hand-held rhythm management device controller are provided, the pulse generating device being implanted within the patient and configured to provide an electrical shock to the patient's heart. At 2404, the patient uses the controller to send a signal to the pulse generating device requesting the current heart rhythm status. At 2406, the pulse generating device responds to the signal from the controller and providing information regarding the status of the heart rhythm to the controller. At 2408, the controller displays the status information to the patient. In an embodiment, the status information from the pulse generating device indicates that the heart's rhythm is within normal parameters. In an embodiment, the status information from the pulse generating device indicates that the heart's rhythm is outside of normal parameters. In an embodiment, the controller further communicates the status information to the patient by an audible human or synthesized voice through a speaker mounted within a case of the controller. In an embodiment, the controller displays that the current heart rhythm is within normal parameters by illuminating an icon visible to the patient on a front of the controller. In an embodiment, the controller further communicates the status information to the patient by an audible human or synthesized voice through a speaker mounted within a case of the controller. In an embodiment, the controller displays the status information that the current heart rhythm is outside normal parameters by illuminating an icon visible to the patient on a front of the controller.

Figure 25:
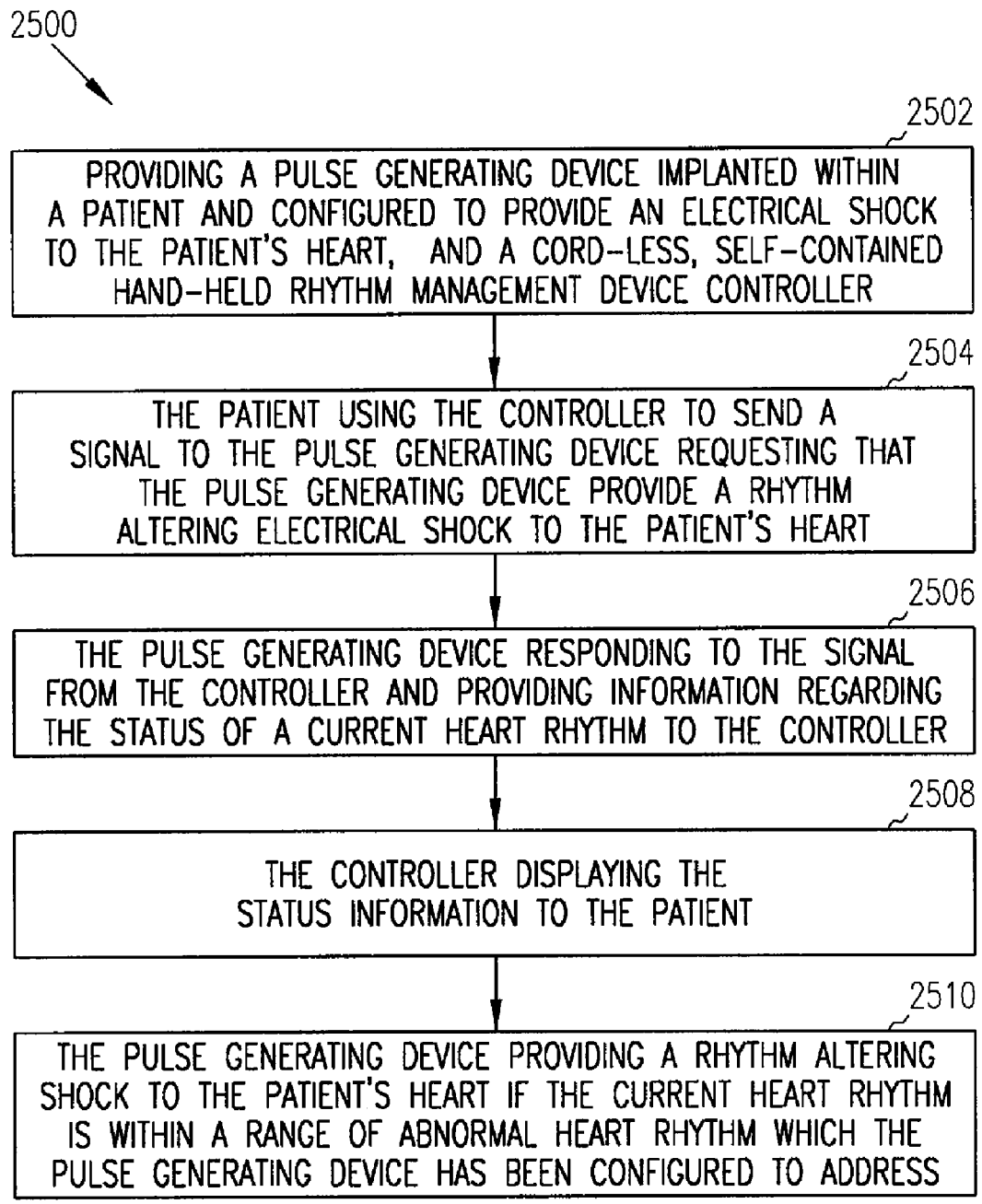
FIG. 25 is a flowchart illustrating a method of requesting therapy.

FIG. 25 is a flowchart illustrating a method 2500 of requesting therapy. At 2502, a pulse generating device and a cord-less, self contained hand-held rhythm management device controller are provided, the pulse generating device being implanted within a patient and configured to provide an electrical shock to the patient's heart. At 2504, the patient uses the controller to send a signal to the pulse generating device requesting that the pulse generating device provide a rhythm altering electrical shock to the patient's heart. At 2506, the pulse generating device responds to the signal from the controller and providing information regarding the status of a current heart rhythm to the controller. At 2508, the controller displaying the status information to the patient. At 2510, the pulse generating device providing a rhythm altering shock to the patient's heart if the current heart rhythm is within a range of abnormal heart rhythm which the pulse generating device has been configured to address. In an embodiment, the current heart rhythm is within a normal range of heart rhythm, the controller displays this normal status to the patient and the pulse generating device does not provide the rhythm altering shock to the patient's heart. In an embodiment, the controller displays the status information that the current heart rhythm is within normal parameters by illuminating an icon visible to the patient on a front of the controller. In an embodiment, the current heart rhythm is outside of a normal range of heart rhythm and not within the range of abnormal heart rhythm the pulse generating device has been configured to address, the controller displays this abnormal status to the patient and the pulse generating device does not provide the rhythm altering shock to the patient's heart. In an embodiment, the controller displays the status information that the current heart rhythm is outside of a normal range of heart rhythm and not within the range of abnormal heart rhythm the pulse generating device has been configured to address by illuminating an icon visible to the patient on a front of the controller. In an embodiment, the current heart rhythm is outside of a normal range of heart rhythm and within the range of abnormal heart rhythm the pulse generating device has been configured to address, the controller displays this abnormal status to the patient and the pulse generating device provides the rhythm altering shock to the patient's heart. In an embodiment, the controller displays the status information that the current heart rhythm is outside of a normal range of heart rhythm but within the range of abnormal heart rhythm the pulse generating device has been configured to address, and that the pulse generating device will deliver a rhythm altering shock to the patient's heart by illuminating an icon visible to the patient on a front of the controller.

Figure 26:
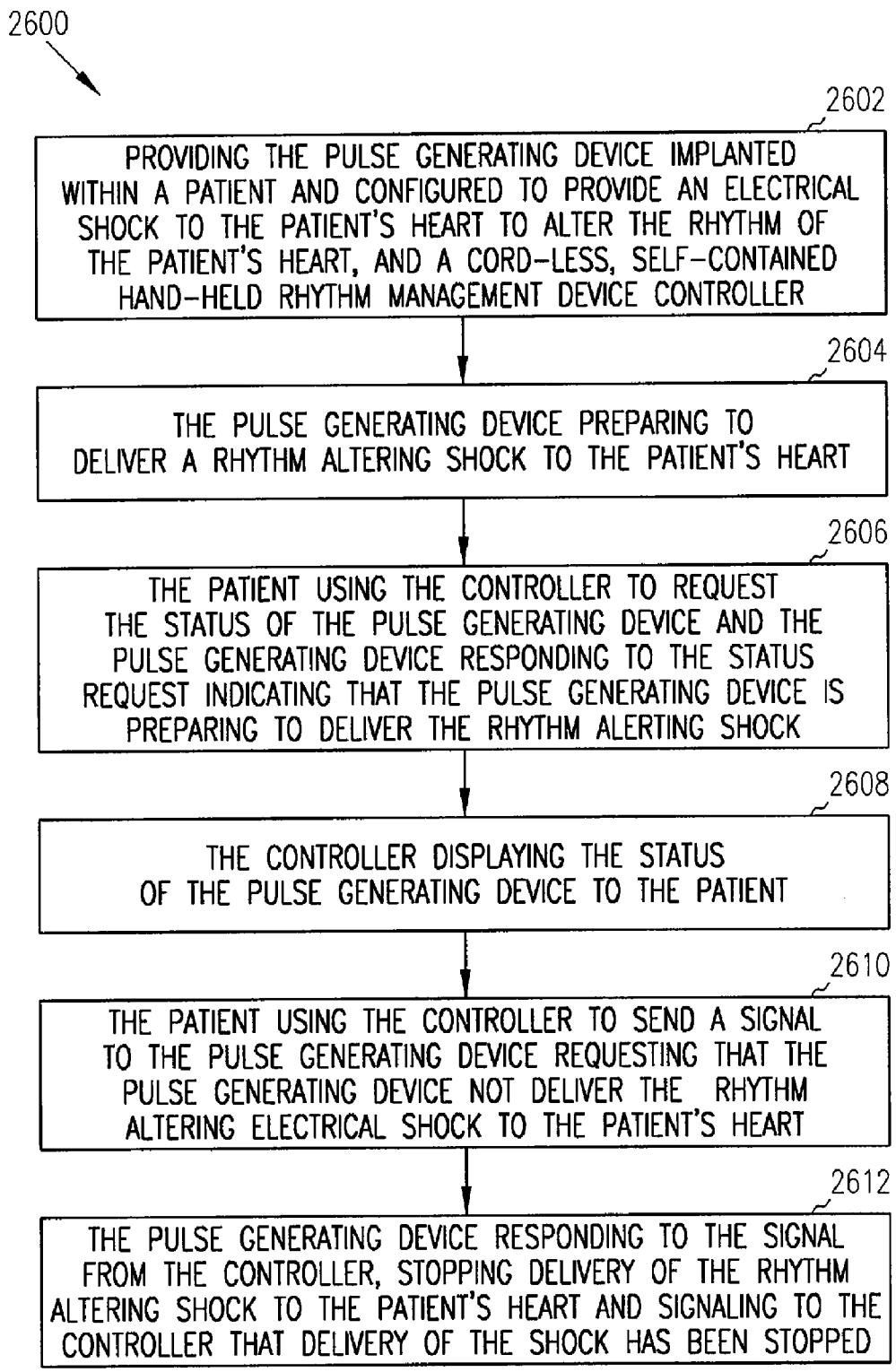
FIG. 26 is a flowchart illustrating a method of preventing a pulse generating device from delivering a rhythm altering shock.

FIG. 26 is a flowchart illustrating a method 2600 of preventing a pulse generating device from delivering a rhythm altering shock. At 2602, the pulse generating device and a cord-less, self-contained hand-held rhythm management device controller are provided, the pulse generating device being implanted within a patient and configured to provide an electrical shock to the patient's heart to alter the rhythm of the patient's heart. At 2604, the pulse generating device is prepared to deliver a rhythm altering shock to the patient's heart. At 2606, the patient uses the controller to request the status of the pulse generating device and the pulse generating device responding to the status request indicating that the pulse generating device is preparing to deliver the rhythm altering shock. At 2608, the controller displays the status of the pulse generating device to the patient. At 2610, the patient uses the controller to send a signal to the pulse generating device requesting that the pulse generating device not deliver the rhythm altering electrical shock to the patient's heart. At 2612, the pulse generating device responds to the signal from the controller, stopping delivery of the rhythm altering shock to the patient's heart and signaling to the controller that delivery of the shock has been stopped.

Having described preferred aspects and embodiments of the present invention, modifications and equivalents of the disclosed concepts may readily occur to one skilled in the art. However, it is intended that such modifications and equivalents be included within the scope of the claims which are appended hereto.

What is claimed is as follows:

1. A method comprising:
providing handheld patient-operated user-interface for an implantable cardiac rhythm management device, the handheld patient-operated user-interface device having a more limited set of commands than a physician-operated user-interface device for the implantable cardiac rhythm management device;
receiving a patient status query at the handheld patient-operated user-interface and, in response to the patient status query, the handheld patient-operated user-interface communicating the patient status query to the implantable cardiac rhythm management device;
receiving, in response to the patient status query, status information at the handheld patient-operated user-interface from the implantable cardiac rhythm management device regarding the rhythm of the patient's heart; and
displaying, using the handheld patient-operated user-interface, the status information obtained from the implantable cardiac rhythm management device, the displaying comprising:
displaying a normal heart rhythm indication when the status information indicates that the rhythm of the patient's heart is in normal rhythm;
displaying an abnormal heart rhythm indication when the status information indicates that the rhythm of the patient's heart is in abnormal rhythm; and
displaying a contact caregiver indication when the status information indicates that some function of the implantable cardiac rhythm management device or the rhythm of the patient's heart is abnormal such that it is advisable for the patient to immediately contact the patient's medical caregiver.

2. The method of claim 1, wherein the displaying the status information includes illuminating an icon visible to the patient on a front of the handheld patient-operated user-interface.

3. The method of claim 1, wherein the displaying the status information includes using a plurality of physically separated deadfront status indicators on the handheld patient-operated user-interface device, the deadfront status indicators comprising: (1) a normal rhythm indicative deadfront status indicator, (2) a contact caregiver indicative deadfront status indicator, and (3) an abnormal rhythm indicative deadfront status indicator, the deadfront status indicators each including a deadfront icon that is illuminated for viewing on a front of the handheld patient-operated user interface.

4. The method of claim 3, wherein the deadfront icons are differentiated from each other by the use of different pictorial graphic shapes that convey information pictographically.

5. The method of claim 3, wherein the displaying the status information obtained from the implantable cardiac rhythm management device includes displaying the status information visually using the deadfront status indicator lamps.

6. The method of claim 3, wherein the displaying the normal heart rhythm indication includes illuminating the normal rhythm indicative deadfront status indicator.

7. The method of claim 3, wherein the displaying the abnormal heart rhythm indication includes illuminating the abnormal rhythm indicative deadfront status indicator.

8. The method of claim 3, wherein the displaying the contact caregiver indication includes illuminating the contact caregiver indicative deadfront status indicator.

9. The method of claim 1, wherein the displaying the status information includes using a plurality of physically separated deadfront status indicators on the handheld patient-operated user-interface device, the deadfront status indicators consisting of: (1) a normal rhythm indicative deadfront status indicator, (2) a contact caregiver indicative deadfront status indicator, and (3) an abnormal rhythm indicative deadfront status indicator, the deadfront status indicators each including a deadfront icon that is illuminated for viewing on a front of the handheld patient-operated user interface.

10. The method of claim 1, including:
receiving, in response to the patient status query, status information at the handheld patient-operated user-interface from the implantable cardiac rhythm management device regarding the status of the implantable cardiac rhythm management device; and
displaying the status information obtained from the implantable cardiac rhythm management device.

11. The method of claim 10, wherein the displaying the status information includes displaying a therapy pending indication when a therapy has been scheduled by the implantable cardiac rhythm management device.

12. The method of claim 11, wherein the displaying the status information includes using a plurality of physically separated deadfront status indicators on the handheld patient-operated user-interface device, the deadfront status indicators comprising: (1) a normal rhythm indicative deadfront status indicator, (2) a contact caregiver indicative deadfront status indicator, (3) an abnormal rhythm indicative deadfront status indicator, and (4) a therapy pending indicative deadfront status indicator, the deadfront status indicators each including a deadfront icon that is illuminated for viewing on a front of the handheld patient-operated user interface.

13. The method of claim 12, wherein the displaying the therapy pending indication includes illuminating the therapy pending indicative deadfront status indicator.

14. The method of claim 11, wherein the displaying the status information includes using a plurality of physically separated deadfront status indicators on the handheld patient-operated user-interface device, the deadfront status indicators consisting of: (1) a normal rhythm indicative deadfront status indicator, (2) a contact caregiver indicative deadfront status indicator, (3) an abnormal rhythm indicative deadfront status indicator, and (4) a therapy pending indicative deadfront status indicator, the deadfront status indicators each including a deadfront icon that is illuminated for viewing on a front of the handheld patient-operated user interface.

15. The method of claim 10, wherein the displaying the status information consists of displaying a therapy pending indication when a therapy has been scheduled by the implantable cardiac rhythm management device.

16. A method comprising:
providing a handheld patient-operated user-interface for an implantable cardiac rhythm management device, the handheld patient-operated user-interface device having a more limited set of commands than a physician-operated user-interface device for the implantable cardiac rhythm management device;
receiving a patient status query at the handheld patient-operated user-interface and, in response to the patient status query, the handheld patient-operated user-interface communicating the patient status query to the implantable cardiac rhythm management device;
receiving, in response to the patient status query, status information at the handheld patient-operated user-interface from the implantable cardiac rhythm management device regarding the rhythm of the patient's heart; and
displaying, using the handheld patient-operated user-interface, the status information obtained from the implantable cardiac rhythm management device, the displaying consisting of:

displaying a normal heart rhythm indication when the status information indicates that the rhythm of the patient's heart is in normal rhythm;

displaying an abnormal heart rhythm indication when the status information indicates that the rhythm of the patient's heart is in abnormal rhythm; and displaying a contact caregiver indication when the status information indicates that some function of the implantable cardiac rhythm management device or the rhythm of the patient's heart is abnormal such that it is advisable for the patient to immediately contact the patient's medical caregiver.

17. A method consisting of:

providing a handheld patient-operated user-interface for an implantable cardiac rhythm management device, the handheld patient-operated user-interface device having a more limited set of commands than a physician-operated user-interface device for the implantable cardiac rhythm management device;

receiving a patient status query at the handheld patient-operated user-interface and, in response to the patient status query, the handheld patient-operated user-interface communicating the patient status query to the implantable cardiac rhythm management device;

receiving, in response to the patient status query, status information at the handheld patient-operated user-interface from the implantable cardiac rhythm management device regarding the rhythm of the patient's heart; and displaying, using the handheld patient-operated user-interface, the status information obtained from the implantable cardiac rhythm management device, the displaying comprising:

displaying a normal heart rhythm indication when the status information indicates that the rhythm of the patient's heart is in normal rhythm;

displaying an abnormal heart rhythm indication when the status information indicates that the rhythm of the patient's heart is in abnormal rhythm; and displaying a contact caregiver indication when the status information indicates that some function of the implantable cardiac rhythm management device or the rhythm of the patient's heart is abnormal such that it is advisable for the patient to immediately contact the patient's medical caregiver.

18. A method comprising:

providing a handheld patient-operated user-interface for an implantable cardiac rhythm management device, the handheld patient-operated user-interface device having a more limited set of commands than a physician-operated user-interface device for the implantable cardiac rhythm management device;

receiving a patient status query at the handheld patient-operated user-interface and, in response to the patient status query, the handheld patient-operated user-interface communicating the patient status query to the implantable cardiac rhythm management device;

receiving, in response to the patient status query, status information at the handheld patient-operated user-interface from the implantable cardiac rhythm management device regarding the rhythm of the patient's heart and the status of the implantable cardiac rhythm management device; and displaying, using the handheld patient-operated user-interface, the status information obtained from the implantable cardiac rhythm management device, the displaying comprising:

displaying a normal heart rhythm indication when the status information indicates that the rhythm of the patient's heart is in normal rhythm;

displaying an abnormal heart rhythm indication when the status information indicates that the rhythm of the patient's heart is in abnormal rhythm;

displaying a contact caregiver indication when the status information indicates that some function of the implantable cardiac rhythm management device or the rhythm of the patient's heart is abnormal such that it is advisable for the patient to immediately contact the patient's medical caregiver; and displaying a therapy pending indication when the status information indicates that a therapy has been scheduled by the implantable cardiac rhythm management device.

19. The method of claim 18, wherein the displaying the abnormal heart rhythm indication includes displaying the abnormal heart rhythm indication when the rhythm of the patient's heart is in abnormal rhythm and no therapy has been scheduled by the implantable cardiac rhythm management device.

20. The method of claim 18, wherein at least one of:

displaying the normal heart rhythm indication includes illuminating a normal rhythm indicative deadfront status indicator having an icon depicting a heart shape;

displaying the contact caregiver indication includes illuminating a contact caregiver indicative deadfront status indicator having an icon depicting a telephone shape;

displaying the therapy pending indication includes illuminating a therapy pending indicative deadfront status indicator having an icon depicting a heart shape with clock face; or displaying the abnormal heart rhythm indication includes illuminating a abnormal rhythm indicative deadfront status indicator having an icon depicting a heart shape with a jagged line extending across the heart.

21. The method of claim 20, wherein the icons are differentiated from each other by the use of different colors provided during the illuminating.

* * * * *